United States Patent
Sachtler

(10) Patent No.: US 7,128,418 B2
(45) Date of Patent: *Oct. 31, 2006

(54) COLOR VISION DEFICIENCY SCREENING TEST RESISTANT TO DISPLAY CALIBRATION ERRORS

(75) Inventor: Wendelin L. Sachtler, Maroubra (AU)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/945,051

(22) Filed: Sep. 20, 2004

(65) Prior Publication Data

US 2005/0036112 A1    Feb. 17, 2005

Related U.S. Application Data

(63) Continuation of application No. 10/277,712, filed on Oct. 22, 2002, now Pat. No. 6,851,809.

(60) Provisional application No. 60/338,950, filed on Oct. 22, 2001.

(51) Int. Cl.
 *A61B 3/02* (2006.01)
 *A61B 3/00* (2006.01)

(52) U.S. Cl. ........................... 351/242; 351/246

(58) Field of Classification Search ............... 351/222, 351/223, 224, 225, 226, 233–236, 237, 239, 351/242, 243, 246
See application file for complete search history.

(56) References Cited

U.S. PATENT DOCUMENTS

| | | | |
|---|---|---|---|
| 3,653,771 A | 4/1972 | Piringer | |
| 3,801,188 A | 4/1974 | Hunt et al. | |
| 3,970,376 A | 7/1976 | Ledl | |
| 4,285,580 A | 8/1981 | Murr | |
| 4,862,265 A | 8/1989 | Bartow et al. | |
| 5,325,136 A | 6/1994 | Salibello et al. | |
| 5,561,459 A | 10/1996 | Stokes et al. | |
| 5,619,349 A | 4/1997 | Ueda et al. | |
| 5,754,222 A | 5/1998 | Daly et al. | |
| 5,799,292 A | 8/1998 | Hekmatpour | |
| 5,864,384 A | 1/1999 | McClure et al. | |
| 5,946,075 A | 8/1999 | Horn | |
| 6,027,217 A | 2/2000 | McClure et al. | |
| 6,203,157 B1 | 3/2001 | Lee | |
| 6,210,006 B1 | 4/2001 | Menozzi | |

FOREIGN PATENT DOCUMENTS

WO    WO 96/39919    12/1996

Primary Examiner—Ali Imam
Assistant Examiner—John R. Sanders
(74) Attorney, Agent, or Firm—Gauthier & Connors LLP

(57) ABSTRACT

A method for testing a plurality of regions in a color space to identify any of, or a subcombination of, the following color vision deficiencies: protanopia, deuteranopia, tritanopia, and related anomalies. A set of distractor colors is distributed across a region of color space such that the confusion line through a single target color intersects approximately the middle of the set. The distractor set spans a region extending in both chromaticity and luminance, which provides leeway for display errors since the confusion line will intersect the set even if colors do not render exactly as specified, and color deficient observers would still not be able to identify the target. A web-based implementation enables remote testing of subjects.

16 Claims, 11 Drawing Sheets
(1 of 11 Drawing Sheet(s) Filed in Color)

COLOR VISION DEFICIENCY SCREENING TEST RESISTANT TO DISPLAY CALIBRATION ERRORS

CROSS-REFERENCE TO OTHER APPLICATIONS

The present application is a continuation application of U.S. patent application Ser. No. 10/277,712 filed on Oct. 22, 2002 now U.S. Pat. No. 6,851,809 which claims priority to U.S. provisional patent application Ser. No. 60/338,950, filed on Oct. 22, 2001.

BACKGROUND OF THE INVENTION

The invention relates to the field of vision testing and, in particular, to a color vision deficiency test using a computer display.

For a number of testing situations, such as remote testing over the Internet, the main challenge is to develop a color vision deficiency test that can provide meaningful assessment in spite of the degradations inherent in uncalibrated and otherwise unknown display devices. Often, performance on psychophysical tests can improve when device miscalibrations lead to artifacts that provide additional cues for the correct target, resulting in a higher false negative rate for detecting sensory deficiencies, meaning that color deficient observers are inappropriately categorized as not having color vision deficiencies. By designing the presentation so that limitations in the display increase the false alarm rate (instead of the false negative rate), a more conservative measure of performance is achieved. The benefit for a screening evaluation is that it is less likely that a person having a sensory deficit will be overlooked, i.e., more people in need of attention will be directed to the appropriate clinicians.

Colors can be described by coordinates in a three-dimensional color space; an example of this is the RGB triplet used to specify colors on a computer monitor. Color vision deficiencies can be characterized by confusion lines in a color space, wherein two colors lying on such a line are difficult or impossible to discriminate from each other by a color deficient observer. Many tests of color vision exploit this phenomenon, and their reliability hinge on the precision with which test colors can be specified. However, if one has only limited control of monitor calibration, as is the case when testing over the Internet, colors displayed at a remote location generally do not render as specified. Color deficient observers could thus pass the test if colors do not fall on a confusion line, which is a disastrous failure mode and one of the main reasons color vision assessment is not generally feasible outside a carefully controlled clinical setting.

There are three major types of color vision deficiencies: protanopia, deuteranopia, and tritanopia, corresponding to an absence or malfunctioning of long, medium, and short wavelength-sensitive cone photoreceptors, respectively. Subcategories of color vision deficiency are the "anomalous" versions of each of the three major categories. The three major categories are characterized by the inability to discriminate colors along particular confusion lines in color space. Anomalies are characterized by greater difficulty, as compared to color normal observers, in discriminating colors along similar confusion lines as the corresponding major deficiencies. Each major type of color vision deficiency requires a test series tailored to its unique set of confusion lines. Each major type of color vision deficiency requires a test series.

SUMMARY OF THE INVENTION

The present invention provides for a method for testing in a plurality of regions in a color space to identify any of, or a subcombination of, the following color vision deficiencies: protanopia, deuteranopia, and tritanopia, as well as related anomalies. In the methodology embodied in the color vision test of the present invention, a set of distractor colors is distributed across a region of color space such that the confusion line through a single target color intersects approximately the middle of the distractor set. The distractor set spans a region extending in both chromaticity and luminance, which provides leeway for display errors since the confusion line will intersect the set even if colors do not render exactly as specified, and color deficient observers would still not be able to identify the target. This provides protection against the most disastrous failure mode.

In an exemplary embodiment, the step of identifying a threshold is based upon a staircase method to adaptively increase the color separation until the subject is able to consistently identify said target color and decrease the color separation until the subject is not able to consistently identify the target color, wherein the threshold is identified based on the upper and lower reversal points of the staircase.

Additionally, in another embodiment, the present invention provides for a web-based color deficiency vision test implemented over a network and rendered on computer displays associated with test subjects.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3b illustrates a close-up, top-down view of the equiluminant plane shown in FIG. 3a.

DETAILED DESCRIPTION OF THE INVENTION

There are a number of ways in which colors displayed on a cathode ray tube (CRT) are likely to deviate from their desired values. Colors shift in ways characteristic of the physical properties of CRT displays, and it is the systematic nature of these color errors that permit incorporation of safeguards in the color screening test proposed here. To our knowledge, no currently available color test explicitly addresses these possible sources of false positive, or worse, false negative, diagnoses. A brief outline regarding some of the most important factors affecting color rendition is now provided.

CRT monitors exhibit characteristic color shifts in the colors they display when they are not calibrated correctly. However, since for a given monitor the chromaticities of the primary colors do not vary significantly with the calibration state, all color shifts must occur within the region of the color space delimited by the primary chromaticities. Thus, if sets of colors within one region of the color space are expanded due to display miscalibration, with the colors contained in the set becoming more discriminable from each other, then sets within other regions of the color space must be compressed, with their colors becoming less discriminable from each other. This phenomenon is exploited in the color test described herein to estimate the calibration state of the display: by testing color discrimination within several regions of the color space (e.g., bluish, greenish, reddish, and around the white point), we can determine if discrimination performance differs across regions as compared to performance by a "normal" observer tested on a fully calibrated monitor.

Luminance output does not increase linearly with voltage applied to a CRT gun, and the nonlinearity is well characterized by a power function, where gamma is an exponent in the range of 2.2 to 2.6. In addition, a luminance pedestal may remain at what is nominally zero voltage. These nonlinearities are commonly corrected by applying the inverse transform through a lookup table. However, using a single, average transform to correct for an average error across all displays means that individual errors will remain for most displays. For optimal correction, the individual monitor must be calibrated. However, since this is best done by using a photometer or similar instrument, it is unlikely that the average computer user will be able to do this.

Figure 1A:
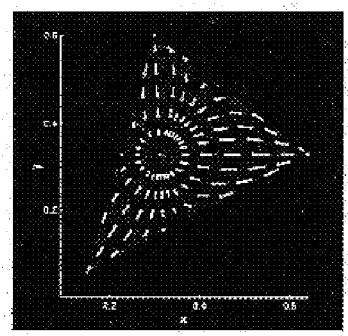
FIG. 1a illustrates the pattern of chromatic shift for gamma=1.2 (undercorrected).
Figure 1B:
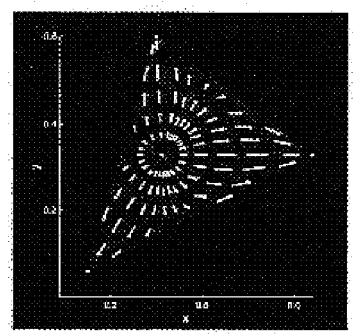
FIG. 1b illustrates the pattern of chromatic shift for gamma=0.8 (overcorrected).

FIGS. 1a and 1b collectively illustrate the pattern of chromatic shifts for various values of gamma. FIG. 1a illustrates the pattern of chromatic shift for gamma=1.2 (undercorrected). FIG. 1b, on the other hand, illustrates the pattern of chromatic shift for gamma=0.8 (overcorrected).

Errors in gamma correction lead to systematic shifts in the displayed colors across the monitor's gamut. For undercorrection, colors shift away from the white point and towards the primary chromaticities, as indicated FIG. 1a. There are three lines (not drawn), emanating from each of the primary chromaticities and passing through the white point, that act as chromatic watersheds—colors on either side of such a line are displaced away from it in the case of undercorrected gamma, or are attracted towards it if gamma is overcorrected. Thus, two colors on either side of such a line will be further apart than their nominal values if gamma is undercorrected and will therefore be more easily discriminable, which is a highly undesirable trait in a color test. It should be noted that colors converge near the vertices of the triangle in the case of undercorrected gamma; this property is exploited in the disclosed color test. For gamma overcorrection (FIG. 1b), the pattern of chromatic shifts is reversed.

Figure 2:
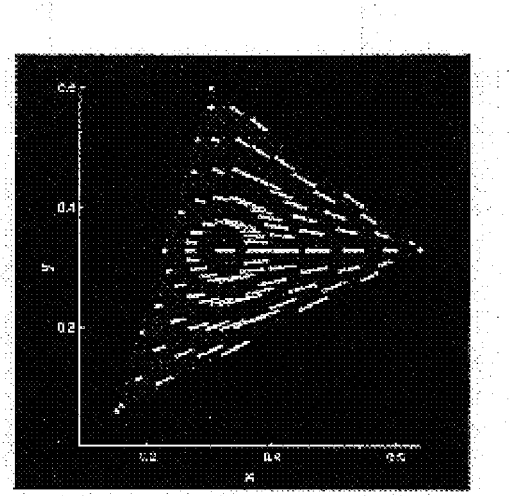
FIG. 2 illustrates the pattern of a red shift.

Monitors have controls to set the color balance. Factory settings may not correspond to a standard white point, and users may well manipulate them. A color deficient observer may choose extreme settings, which could strongly bias test results either to facilitate diagnosis or to misdirect it. FIG. 2 shows an example of a red shift. Note that the pattern of chromatic shifts is systematic, with regions of divergence and convergence. This pattern can be used to identify color shifts since colors in one part of the space will be more easily discriminable than in other parts.

The present invention provides for a method and a system that overcomes such calibration problems in display devices by testing color discrimination within several regions of a color space and determining if a test subject has any of the above-mentioned color deficiencies (protanopia, deuteranopia, and tritanopia).

Figure 3A:
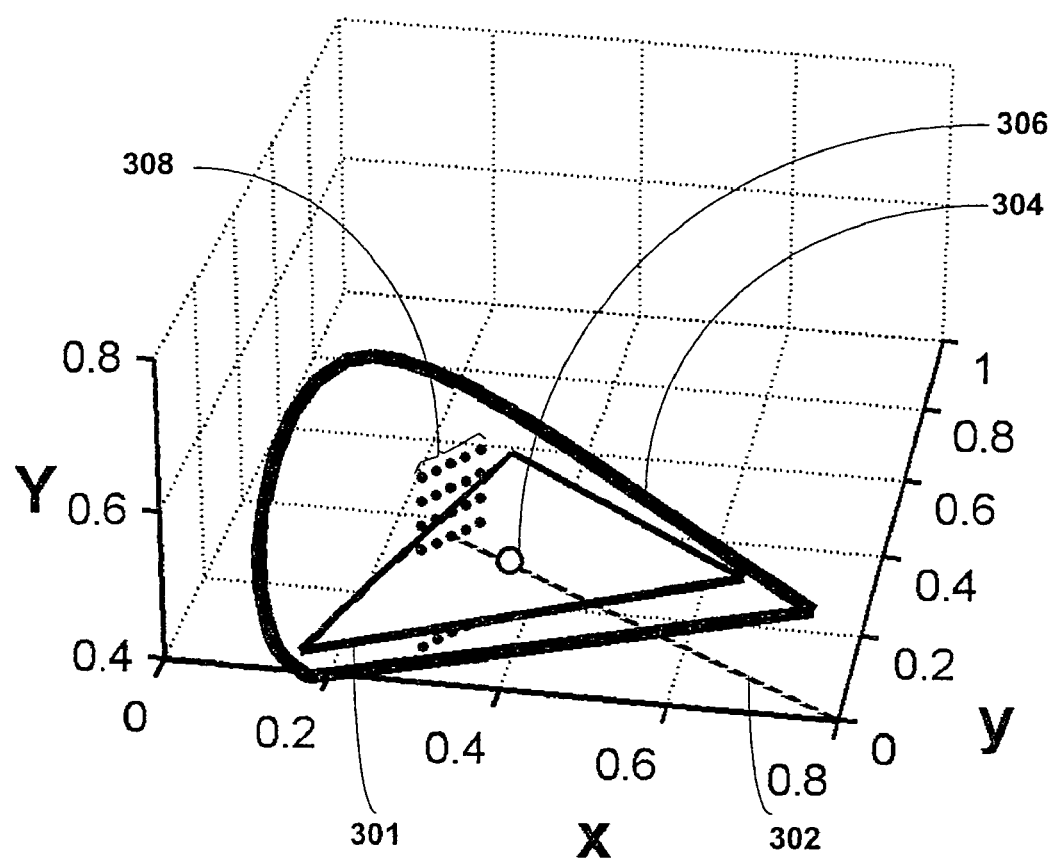
FIG. 3a illustrates the present invention methodology for selection of colors within a color space.

FIG. 3a illustrates a selection of colors within a color space. Triangle 301 shows the range of colors obtainable on a CRT monitor as plotted on a CIE diagram (a standard rendering of color space), shown as a horseshoe-shaped thick curve 304. Additionally, in the example, one of the confusion lines 302 for a deuteranope is shown. The target color 306 (large white dot, outlined with a black border) is chosen to lie on the confusion line. A distractor set of colors (shown as an array of dots 308) is chosen so that it extends above and below the luminance plane shared with the target, and is placed so the confusion line passing through the target color also passes approximately through the middle of the set.

Figure 3B:
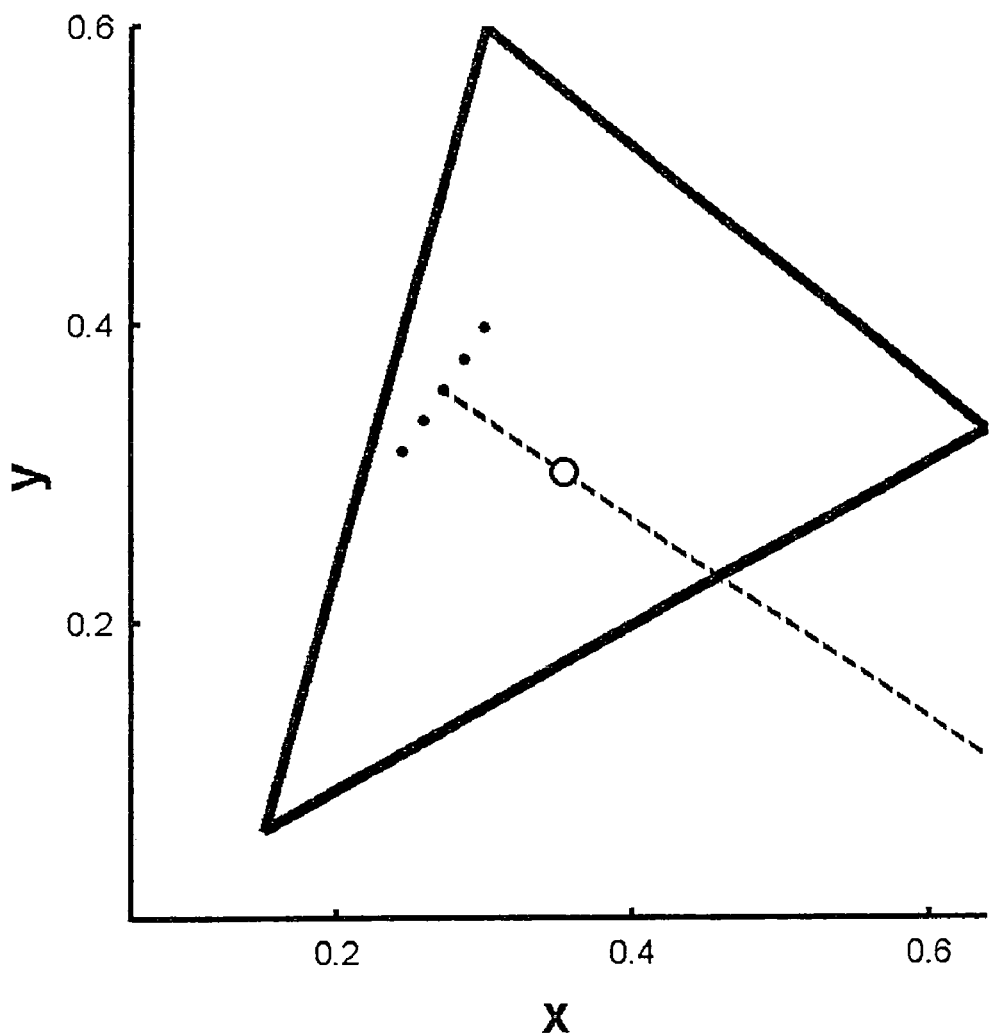

FIG. 3b shows a close-up, top-down view of the equiluminant plane shown in FIG. 3a. The confusion line passing through the target color (large circle) intersects roughly the centroid of the distractor color set (shown as a row of dots). This distractor set is approximately aligned with the plane normal to the confusion line.

Greater separation between the target color and the distractor set makes identification of the target easier, while smaller separations make identification more difficult.

Figure 4:
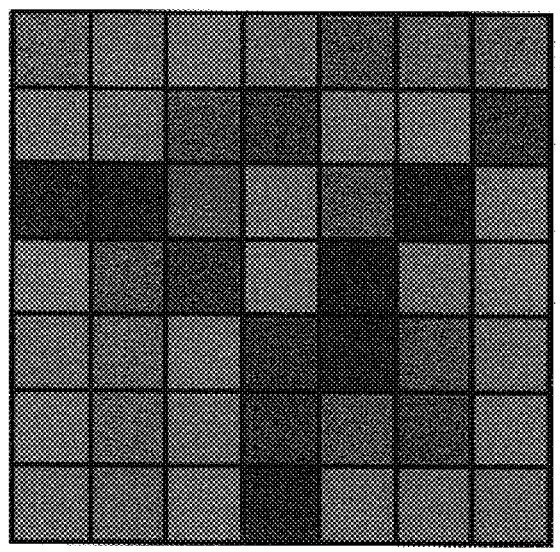
FIG. 4 illustrates an example showing the appearance of the test plate.

FIG. 4 illustrates an example showing the appearance of a test plate. Distractor colors are quasi-randomly assigned to different patches in a visual display. The target color is assigned to a patch at a quasi-randomly selected location of the display on each trial. An actual test plate rendered on a subject's display device is in color, with one square in the test plate representing the target color. Since the luminance of the target element lies within the luminance distribution of the distractor set, the target is distinguishable from the distractor set only by chromaticity.

The present invention is implemented, in one embodiment, using a software engine, based on standard methods, which chooses the stimulus parameters to be tested on any given trial and initiates the next trial. The stimulus sequence engine also keeps track of completed trials and all conditions, and it stores all the data. The test is completed when thresholds have been measured for all conditions.

The test can be administered as a fixed number of conditions that are presented to each observer. The conditions are described in sections A, B, and C below. In this case, the total number of trials equals the number of conditions in A times the number of conditions in B times the number of conditions in C.

A: Different Types of Color Vision Deficiencies

At least three separate test sequences are necessary to determine if an observer exhibits any of the three major categories of color vision deficiency or their subcategories.

B: Testing within Several Regions of Color Space

Figure 5A:
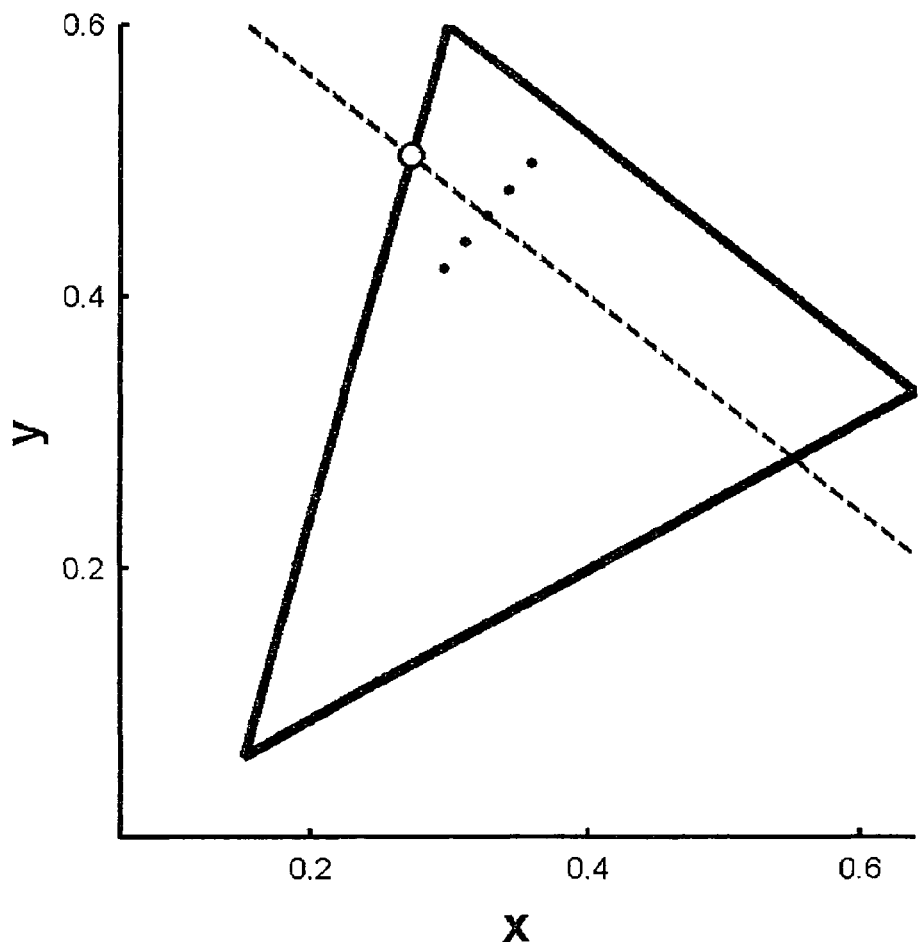
FIGS. 5a–c collectively illustrate the present invention's methodology for testing within several regions of the color space.
Figure 5B:
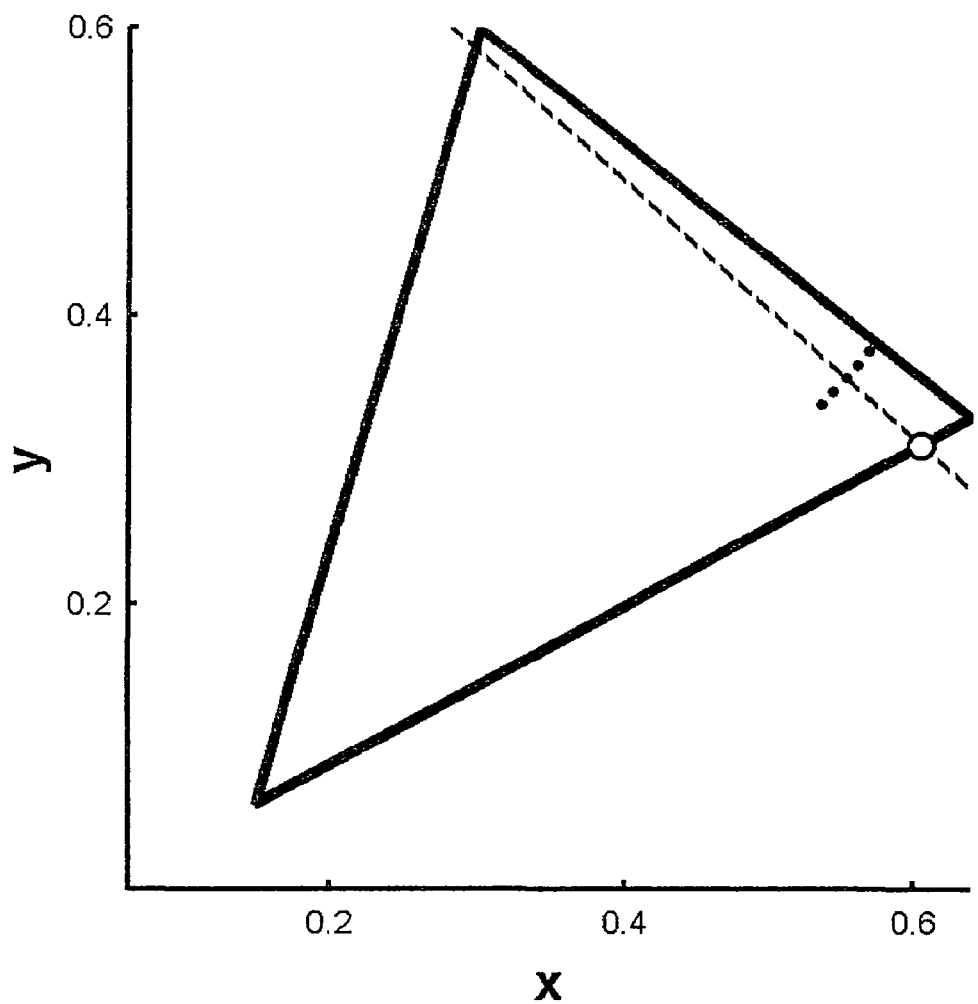
Figure 5C:
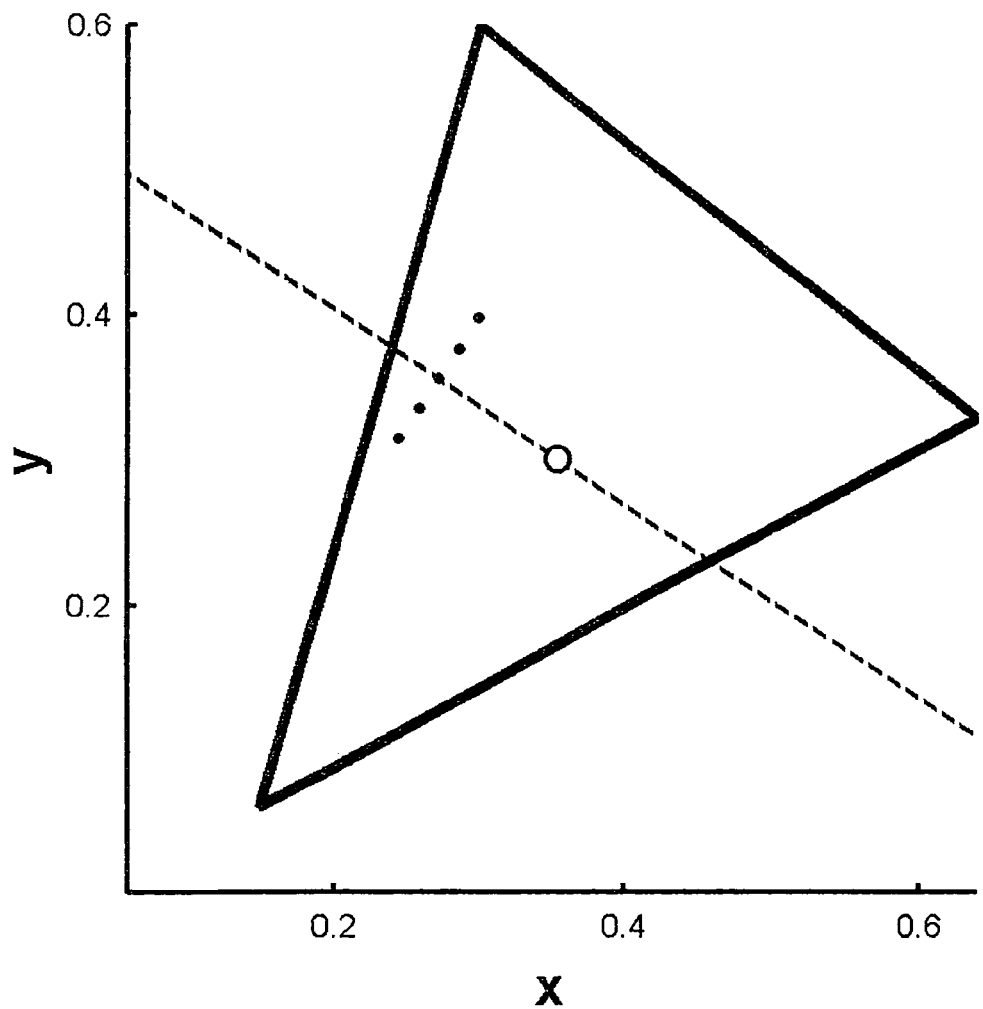

Each test sequence in A must be repeated in several regions of color space (3 or 4 regions are probably sufficient). FIGS. 5a–c collectively illustrate testing within several regions of the color space. FIG. 5a illustrates a specific instance wherein the test sequence is performed in the region corresponding to the green color. FIG. 5b, on the other hand, corresponds to a test sequence that is repeated in the region corresponding to the red color. Lastly, FIG. 5c illustrates the test sequence as repeated around the region corresponding to the white point (not shown).

C: Trials to Measure Threshold to Identify the Target within Distractor Set

The chromaticity of the target color differs from the average (or centroid) of the chromaticities of the colors in the distractor set. The separation between the target color and the distractor centroid is varied in the color test to measure the observer's ability to identify the target color within the distractor set. This can be done with any number of standard threshold measurement methods. For example, the staircase method adaptively increases the value of the color separation as long as an observer is not able to consistently identify the target color, and decreases the separation again until the observer is no longer able to consistently identify the target. This is repeated a number of times, and the average of the upper and lower staircase reversal points is used as an estimate of the detection threshold.

The color test can be implemented using a fixed number of staircase reversals. After completion, the variance of the reversal points is calculated, and the value of the average, representing the threshold, is accepted if the variance is below a chosen value. Otherwise, the test is deemed inconclusive, and the observer can be asked to seek further testing, or the test may be repeated with an equal or larger number of reversals.

A user's thresholds are compared to a database of average thresholds for a population of color normal observers tested on fully calibrated monitors. A user passes a particular subtest if the thresholds are less than or equal to the corresponding thresholds for the normal comparison population, or if they are no greater than a statistical criterion value based on the variance of the measurements. An observer is deemed to have functional color vision if he or she passes all subtests within the master color test battery. Otherwise, the user is urged to seek further testing.

Figure 6:
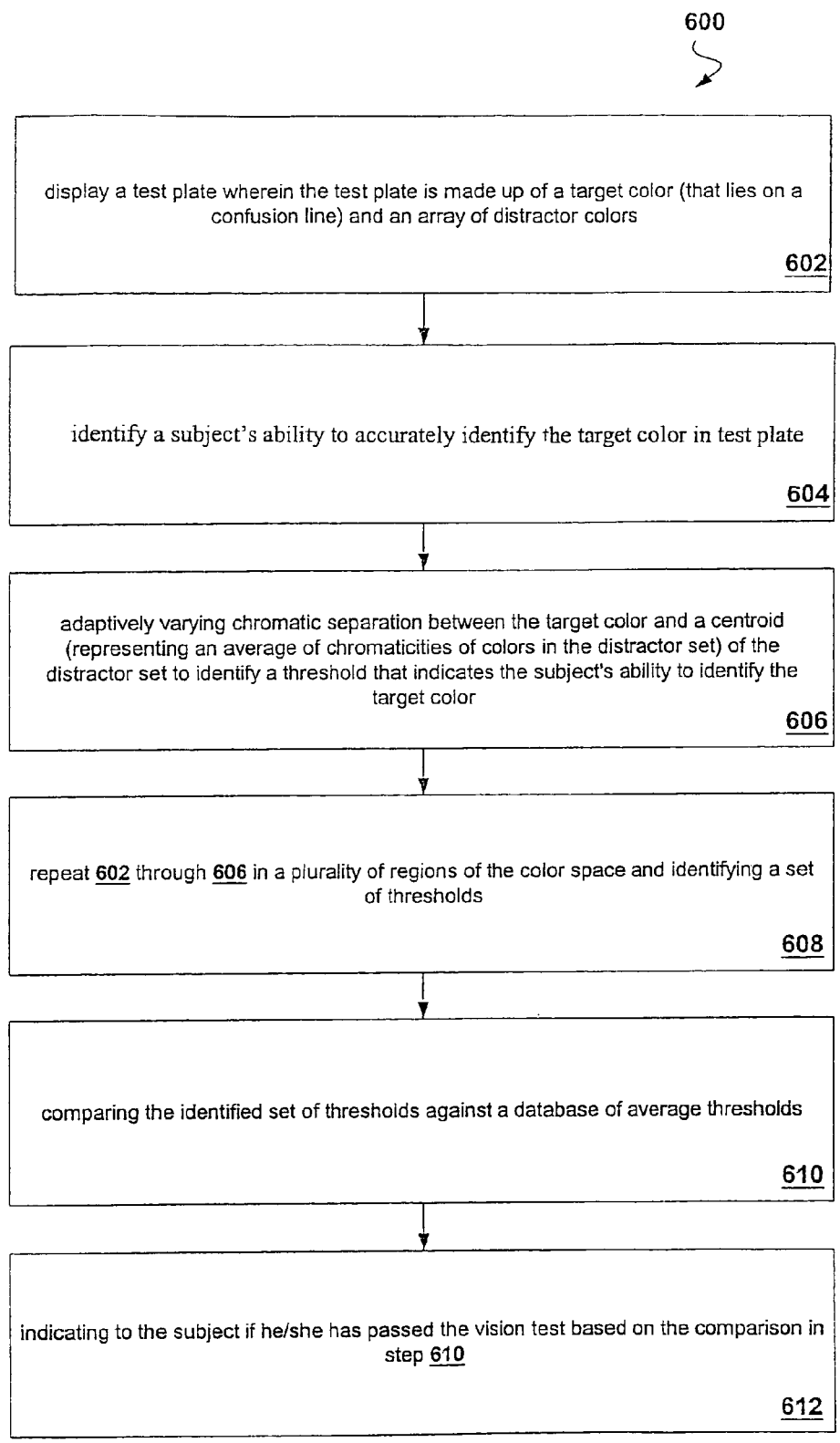
FIG. 6 illustrates an exemplary embodiment associated with the present invention's method for testing a plurality of regions in a color space to identify color vision deficiencies.

FIG. 6 illustrates an exemplary embodiment associated with the method 600 of the present invention for testing in a plurality of regions in a color space to identify any of, or a subcombination of, or anomalies related to, the following color vision deficiencies: protanopia, deuteranopia, and tritanopia. The method comprises the following steps:

Step 602: A test plate is displayed in this step, wherein the test plate made up of a target color and an array of distractor set of colors, and the target color selected to lie on a confusion line associated with any of said color vision deficiencies. The target and distractor colors are re-assigned to random locations on each trial.

Step 604: A subject's ability to accurately identify the target color in the test plate is identified.

Step 606: Vary, adaptively, the chromatic separation between the target color and a centroid (said centroid representing an average of chromaticities of colors associated with said distractor set) of the distractor set of colors to help identify a threshold that defines the subject's ability to identify the target color;

Step 608: Repeat steps 602 through 606 in a plurality of regions in said color space and identifying a set of thresholds.

Step 610: Compare the identified set of thresholds against a database of average thresholds corresponding to subjects tested on calibrated display device.

Step 612: If the identified thresholds are greater than corresponding thresholds in the database, then indicate to the subject the presence of color deficiency corresponding to the target color (depending on which confusion line the target color is on).

It should be noted that the steps of the above-described method are repeated with a different test plate to identify the presence/absence of any of the three color deficiencies (or their sub-combinations or variants).

Figure 7:
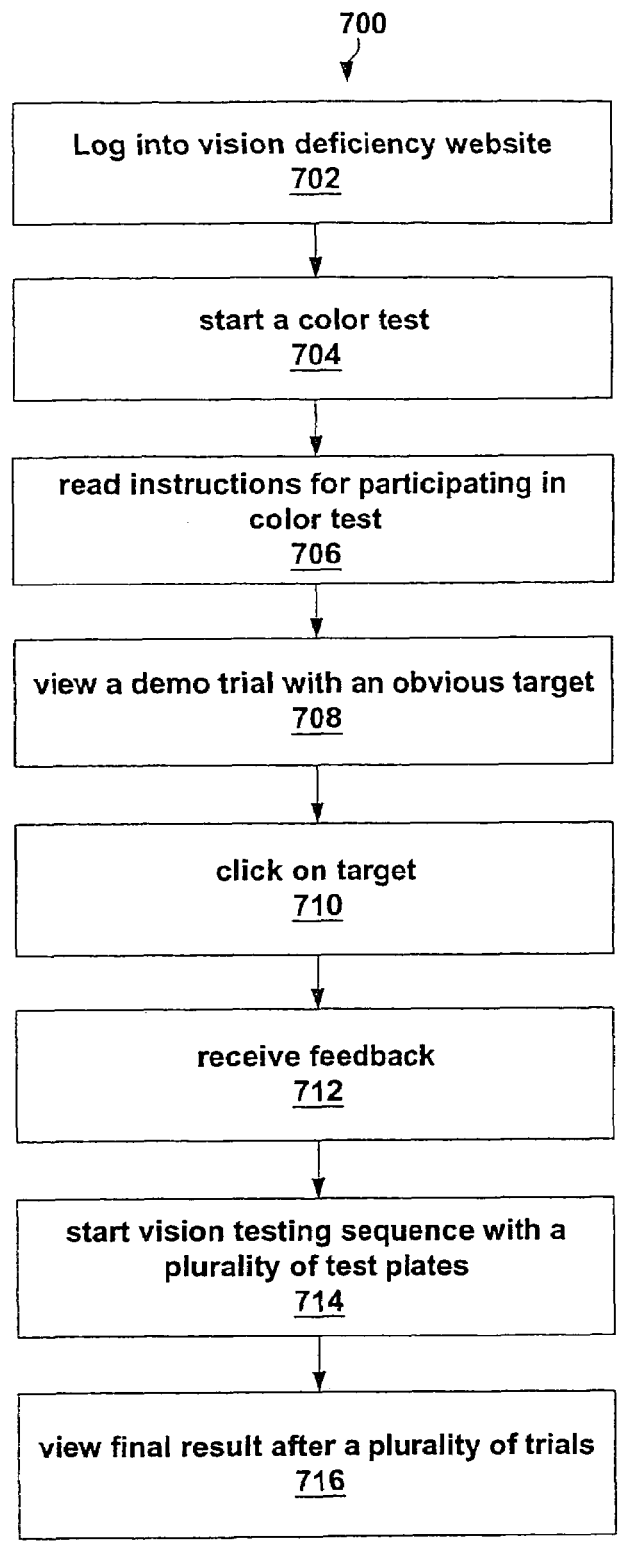
FIG. 7 illustrates a method outlining an exemplary application of the present invention.

FIG. 7 illustrates a method 700 outlining an exemplary application of the present invention, wherein the method 700 includes the steps of: (a) logging in to a website (step 702); (b) starting a color test (step 704); (c) reading instructions (step 706) such as: "Click on the element in the mosaic whose color is most different from the other elements in the group"; (d) viewing a demo trial (step 708) with an obvious target (colors chosen so that they do not lie on any of the major confusion lines and the target is of greatly different luminance from all the elements in the distractor set); (e) clicking on the target (step 710); (f) receiving feedback (step 712) (e.g., a light-enhanced outline, a tone signal, or a spoken or written "ok" vs. "incorrect" message); (g) starting vision test and repeating this sequence for a series of images and, after a number of trials (step 714), and (h) receiving the result (step 716): "Color vision ok." or "Please seek further testing".

Figure 8:
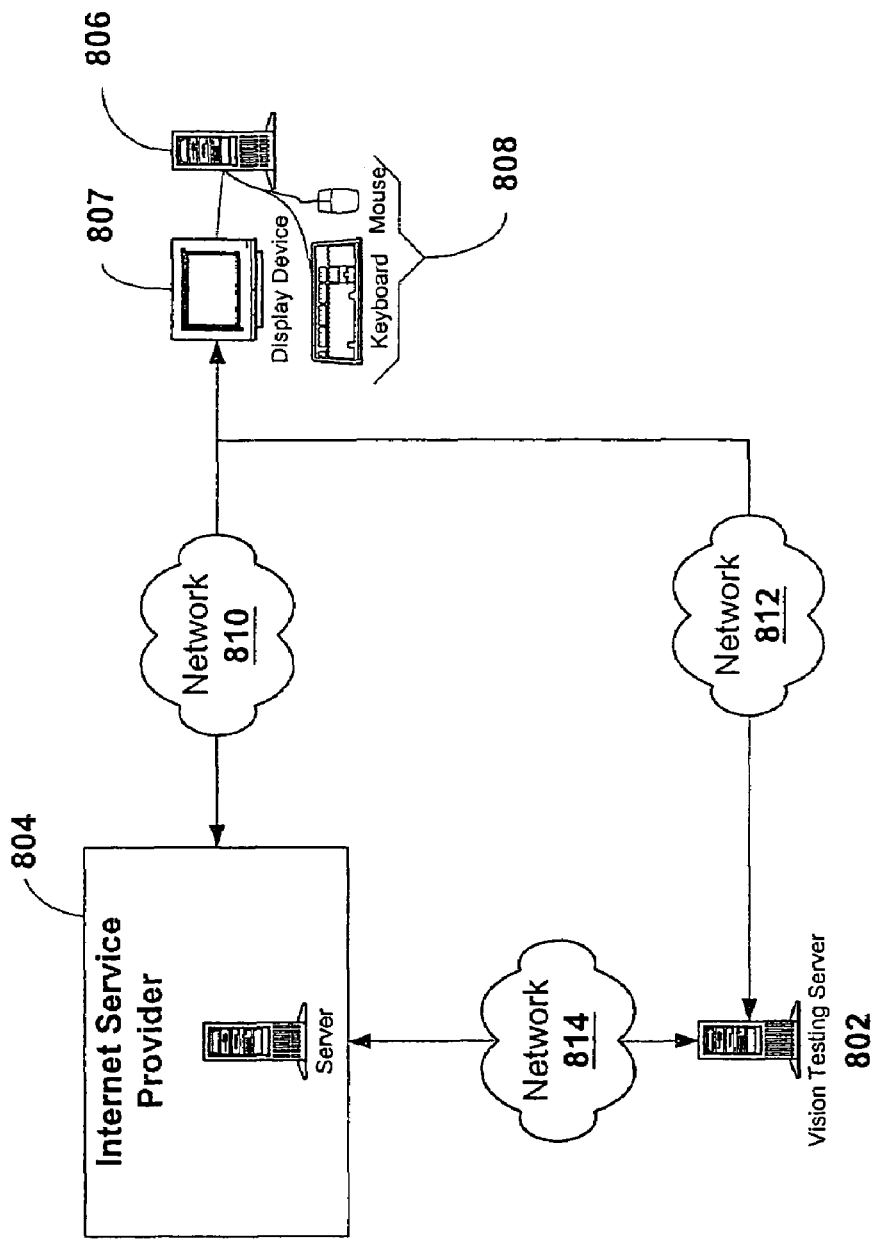
FIG. 8 illustrates a system implementing the present invention's vision testing method via a stand-alone vision testing server or a vision testing server working in conjunction with an Internet Service Provider (ISP).

FIG. 8 illustrates a system implementing the present invention's vision testing method via a stand-alone vision testing server 802 or a vision testing server working in conjunction with an Internet Service Provider (ISP) 804. On the client's (subject's) side, equipment to implement the method of the present invention include, but are not limited to: a computer 806, a display device 807 such as a cathode ray tube (CRT) display monitor, an input device 808 such as a mouse and/or keyboard, and a communication link for accessing data related to the vision test over a network 810, 812. Thus, in one embodiment, the user is able to directly access vision testing server 802 over network 812. In another embodiment, the user is able to access vision testing server 802 via ISP 804 (which in turn is able to access the vision testing server over network 814). The network cloud (810, 812, 814) shown in FIG. 8 could be any of, or a combination of, the following (but not limited to) networks: local area networks (LANs), wide area networks (WANs), or the Internet. Thus, the vision test can be administered over a network such as the World Wide Web as long as the subject has access to such a network and a web browser to run the test. Additionally, the method can be implemented using a variety of Internet access protocols. On the host side, a software module controls the sequence of test presentations, data collection, and test evaluation.

Furthermore, the present invention includes computer program code, which is stored on a storage medium and which can be used to instruct a computer to perform any of the methods associated with the present invention. The computer storage medium includes any of, but is not limited to, the following: CD-ROM, DVD, magnetic tape, optical disc, hard drive, floppy disk, ferroelectric memory, flash memory, ferromagnetic memory, optical storage, charge coupled devices, magnetic or optical cards, smart cards, EEPROM, EPROM, RAM, ROM, DRAM, SRAM, SDRAM, and/or any other appropriate static or dynamic memory or data storage device.

Implemented in the computer readable program code are software modules for computer readable program code for: (a) displaying a test plate, said test plate made up of a target color and an array of distractor set of colors, said target color selected to lie on a confusion line associated with any of said color vision deficiencies; (b) identifying a subject's ability to accurately identify said target color in said test plate; (c) adaptively varying chromatic separation between said target color and a centroid of said distractor set of colors to identify a threshold that identifies said subject's ability to identify said target color, said centroid representing an average of chromaticities of colors associated with said distractor set; (d) repeating steps a–c in a plurality of regions in said color space and identifying a set of thresholds; (e) comparing said identified set of thresholds against a database of average thresholds corresponding to subjects tested on a calibrated display device and, if said identified threshold is less than a corresponding threshold in said database, indicating to said subject an absence of color deficiency corresponding to said target color; and (f) repeating steps a–e with a different test plate to identify any of said color deficiencies.

Although the present invention has been shown and described with respect to several preferred embodiments thereof, various changes, omissions, and additions to the form and detail thereof may be made therein without departing from the spirit and scope of the invention.

What is claimed is:

1. A color deficiency vision test implemented on a computer and a medium capable of rendering a range of colors defined by a color space, said computer being associated with a test subject, said test comprising the steps of:
   a. selecting a confusion line associated with a particular color vision deficiency;
   b. selecting a set of distractor colors extending in luminance, or chromaticity, or both luminance and chromaticity, said distractor set oriented so it is approximately aligned with the plane normal to said confusion line and intersected approximately at its centroid or within its convex hull by said confusion line, extending above, or below, or above and below, or lying on, the luminance plane on which said confusion line is located;
   c. selecting a target color in said color space, said target color separated from said distractor set by a chromatic separation along said confusion line associated with a particular color vision deficiency;
   d. quasi-randomly assigning the distractor and target colors to locations in a test plate;
   e. rendering a plurality of modified test plates to test for color vision deficiency corresponding to said target color, said modification based upon varying the distance between said distractor set and said target color; and
   f. repeating steps c–d in multiple regions of said color space and identifying the presence or absence of said particular color vision deficiency.

2. A color deficiency vision test implemented on a computer and a medium capable of rendering a range of colors defined by a color space, said computer being associated with a test subject, as per claim 1, wherein said identification for the presence or absence of said particular color vision deficiency is based upon a threshold associated with said variance in the distance between said distractor set and said target color.

3. A color deficiency vision test implemented on a computer and a medium capable of rendering a range of colors defined by a color space, said computer being associated with a test subject, as per claim 2, wherein said threshold is identified via an adaptive method, said adaptive method comprising the steps of:
   a. adaptively increasing said distance between said distractor set and said target color to identify a set of upper range points where said test subject is able to identify said target color;
   b. adaptively decreasing distance between said distractor set and said target color to identify a set of lower range points where said test subject is unable to identify said target color; and
   c. identifying said threshold based upon an average of said upper range points and lower range points.

4. A color deficiency vision test implemented on a computer and a medium capable of rendering a range of colors defined by a color space, as per claim 1, wherein said color deficiencies are any of, a sub-combination of, or related anomalies of the following: protanopia, deuteranopia, or tritanopia.

5. A color deficiency vision test implemented over a network and rendered on a medium capable of displaying a range of colors defined by a color space, said network-based color deficiency test comprising the steps of:
   a. receiving a request for a network-based color deficiency vision test from a test subject over said network; transmitting instructions over said network to a computing device associated with said test subject and said medium, said instructions:
      i. identifying a target color, said target color selected to lie on or near a confusion line associated with a particular color vision deficiency;
      ii. identifying or creating a test plate comprising said target color and an array of distractor colors, said distractor set extending above, or below, or above and below, or lying on, a luminance plane shared with said target color in said color space, said target color separated from the color set in said array by a chromatic separation;
      iii. aiding said medium in rendering a plurality of modified test plates, said modified test plates testing for color vision deficiency corresponding to said target color, said modification based upon varying the distance between said distractor set and said target color; and
   b. transmitting instructions for repeating steps i–iii in multiple regions of said color space and identifying the presence or absence of said particular color vision deficiency.

6. A color deficiency vision test implemented over a network and rendered on a medium capable of displaying a range of colors defined by a color space, as per claim 5, wherein said color deficiencies are any of, a sub-combination of, or related anomalies of the following: protanopia, deuteranopia, or tritanopia.

7. A color deficiency vision test implemented over a network and rendered on a medium capable of displaying a range of colors defined by a color space, as per claim 5, wherein said identification of the presence or absence of said particular vision deficiency is based upon a threshold associated with said variance in the distance between said distractor set and said target color.

8. A color deficiency vision test implemented over a network and rendered on a medium capable of displaying a range of colors defined by a color space, as per claim 7, wherein said threshold is identified via an adaptive method, said adaptive method comprising the steps of:
   a. adaptively increasing said distance between said distractor set and said target color to identify a set of upper range points where said test subject is able to identify said target color;
   b. adaptively decreasing distance between said distractor set and said target color to identify a set of lower range points where said test subject is unable to identify said target color; and c. identifying said threshold based upon an average of said upper range points and lower range points.

9. A method for testing and identifying color vision deficiencies associated with a test subject, said method comprising the steps of:
   a. displaying a test plate in a medium capable of rendering a range of colors defined by a color space, said test plate comprising a target color and an array of distractor colors, said distractor set extending above, or below, or above and below, or lying on a luminance plane shared with said target color in said color space, said target color selected to lie on a confusion line associated with a particular color vision deficiency, said target color separated from said distractor set by a chromatic separation;
   b. adaptively varying said chromatic separation between said target color and the centroid of said distractor set of colors a plurality of times to identify an average threshold that identifies said test subject's ability to identify said target color in said test plate, said centroid representing an average of said distractor set's color coordinates in said color space; and
   c. comparing said identified average threshold against a database of average thresholds corresponding to subjects tested on a standardized display medium and, if said identified average threshold is greater than corresponding average threshold in said database, indicating to said test subject the presence of said particular color deficiency corresponding to said target color.

10. A method for testing and identifying color vision deficiencies associated with a test subject, as per claim 9, wherein steps a–c are repeated using a plurality of target colors lying in different confusion lines to identify the presence of other color vision deficiencies.

11. A method for testing and identifying color vision deficiencies associated with a test subject, as per claim 9, wherein said average threshold is identified via an adaptive method, said adaptive method comprising the steps of:
   a. adaptively increasing said chromatic separation to identify a set of upper range points where said subject is able to identify said target color;
   b. adaptively decreasing said chromatic separation to identify a set of lower range points where said subject is unable to identify said target color; and
   c. identifying said average threshold based upon an average of said upper range points and lower range points.

12. A method for testing and identifying color vision deficiencies associated with a test subject, as per claim 9, wherein said color deficiencies are any of, a sub-combination of, or related anomalies of the following: protanopia, deuteranopia, or tritanopia.

13. An article of manufacture comprising a computer usable medium having computer readable program code embodied therein for testing and identifying color vision deficiencies associated with a test subject, said medium comprising:
   a. computer readable program code aiding in displaying a test plate in a medium capable of rendering a range of colors defined by a color space, said test plate comprising a target color and an array of distractor colors, said distractor set extending above, or below, or above and below, or lying on, a luminance plane shared with said target color in said color space, said target color selected to lie on a confusion line associated with a particular color vision deficiency, said target color separated from said distractor set by a chromatic separation;
   b. computer readable program code adaptively varying said chromatic separation between said target color and a centroid of said distractor set of colors a plurality of times to identify an average threshold that identifies said test subject's ability to identify said target color in said test plate, said centroid representing an average of said distractor set's color coordinates in said color space; and
   c. computer readable program code comparing said identified average threshold against a database of average thresholds corresponding to subjects tested on a standardized display medium and, if said identified average threshold is greater than corresponding average threshold in said database, indicating to said test subject the presence of said particular color deficiency corresponding to said target color.

14. An article of manufacture comprising a computer usable medium having computer readable program code embodied therein for testing and identifying color vision deficiencies associated with a test subject, as per claim 13, wherein said average threshold is identified via an adaptive method, said adaptive method as implemented in computer readable program code comprising the steps of:
   a. adaptively increasing said chromatic separation to identify a set of upper range points where said subject is able to identify said target color;
   b. adaptively decreasing said chromatic separation to identify a set of lower range points where said subject is unable to identify said target color; and
   c. identifying said average threshold based upon an average of said upper range points and lower range points.

15. A method for testing a test subject for one or more color vision deficiencies via a medium capable of rendering a range of colors defined by a color space, said method implemented over a network, said method comprising the steps of:
   a. receiving a request for testing one or more color deficiencies over said network;
   b. transmitting data over said network for rendering a test plate in said medium, said test plate comprising a target color and an array of distractor colors, said distractor set extending above, or below, or above and below, or lying on, a luminance plane shared with said target color in said color space, said target color selected to lie on a confusion line associated with a particular color vision deficiency, said target color separated from said distractor set by a chromatic separation;
   c. transmitting instructions over said network for adaptively varying said chromatic separation between said target color and a centroid of said distractor set of colors a plurality of times to identify an average threshold that identifies said test subject's ability to identify said target color in said test plate, said centroid representing an average of said distractor set's color coordinates in said color space;
   d. receiving said identified average threshold;
   e. accessing a database and comparing said identified average threshold against a corresponding average threshold value in said database, said average threshold values in said database corresponding to subjects tested on a standardized display medium; and
   f. if said identified average threshold is greater than corresponding average threshold in said database, transmitting an indicator to said test subject indicating the presence of said particular color deficiency corresponding to said target color.

16. A method for testing a test subject for one or more color vision deficiencies via a medium capable of rendering a range of colors defined by a color space, said method implemented over a network, as per claim 15, wherein said color deficiencies are any of, a sub-combination of, or related anomalies of the following: protanopia, deuteranopia, or tritanopia.

* * * * *